United States Patent [19]

Halpern et al.

[11] Patent Number: 5,106,984
[45] Date of Patent: Apr. 21, 1992

[54] 2-HYDROCARBYL-3,6-DICHLOROPYRIDINES AND THEIR PREPARATION

[75] Inventors: Marc E. Halpern, Midland, Mich.; Jon A. Orvik, Walnut Creek; Thomas J. Dietsche, Berkeley, both of Calif.

[73] Assignee: The Dow Chemical Company, Midland, Mich.

[21] Appl. No.: 18,250

[22] Filed: Feb. 24, 1987

Related U.S. Application Data

[63] Continuation-in-part of Ser. No. 811,850, Dec. 20, 1985, abandoned.

[51] Int. Cl.$^5$ ............... C07D 213/61; C07C 253/30; C07C 255/03
[52] U.S. Cl. .................... 546/250; 546/345; 558/303; 558/368; 558/371; 558/430; 558/432; 558/433; 558/434; 558/440
[58] Field of Search .............. 558/440, 371, 368; 546/250, 345

[56] References Cited

U.S. PATENT DOCUMENTS

| | | | |
|---|---|---|---|
| 2,679,453 | 5/1954 | Brett et al. | 71/2.5 |
| 2,850,519 | 9/1958 | Krimm | 260/464 |
| 3,135,594 | 6/1964 | Goring | 71/11 |
| 3,244,722 | 4/1966 | Johnson et al. | 260/294.8 |
| 3,317,549 | 5/1967 | Johnson | 260/294.9 |
| 3,480,661 | 11/1969 | Rust et al. | 560/219 X |
| 4,245,098 | 1/1981 | Steiner et al. | 546/250 |
| 4,435,573 | 3/1984 | Lysenko et al. | 546/250 |
| 4,469,896 | 9/1984 | Steiner et al. | 568/495 |
| 4,474,602 | 10/1984 | Markley et al. | 71/94 |
| 4,584,380 | 4/1986 | Hartmann | 546/250 |

FOREIGN PATENT DOCUMENTS

| | | |
|---|---|---|
| 0046735 | 3/1982 | European Pat. Off. ........... 546/250 |
| 0078234 | 5/1983 | European Pat. Off. . |
| 1492103 | 11/1977 | United Kingdom . |

OTHER PUBLICATIONS

Morrison and Boyd, Organic Chemistry, 4th Ed., pp. 747–748, Allyn & Bacon, Ltd., Boston-London-Sydney-Toronto.
Abramovitch; Pyridine & its Derivatives; Supp. PSO. 2(1974), pp. 308–311.
Abramovitch; Pyridine & its Derivatives; Supp. PSO. 3(1974), pp. 268–272.
Coppens; et al., C.A., 78, 71335j (1973).
Albertson; J.A.C.S., 74, (1952), pp. 3816–3818.
Yogi, et al.; Chemistry Letters, (1982), pp. 1579–1582.
Steiner, et al., Helv. Chem. Acta., 65(1982), pp. 983–985.
C.A., 1972–1976 Chem. Substance Index, pp. 33611CS and 33613CS.
Van Der Does, et al., C.A. 78(1973), 84219z.

*Primary Examiner*—Joseph Paul Brust
*Attorney, Agent, or Firm*—D. Wendell Osborne

[57] ABSTRACT

2-Hydrocarbyl-3,6-dichloropyridines are prepared from dichloromethyl hydrocarbyl ketones and acrylonitrile in a two-step process involving an addition reaction under basic conditions to form intermediate 1,1-dichloro-3-cyanopropyl hydrocarbyl ketones and a subsequent cyclization reaction in the presence of hydrogen chloride. Thus, 3,6-dichloro-2-methylpyridine is prepared from 1,1-dichloro-2-propanone and acrylonitrile by the formation and further reaction of 4,4-dichloro-5-oxo-hexanenitrile. The intermediates and products are novel compounds useful in the preparation of herbicides and nitrification inhibitors.

18 Claims, No Drawings

2-HYDROCARBYL-3,6-DICHLOROPYRIDINES AND THEIR PREPARATION

CROSS-REFERENCE TO RELATED APPLICATIONS

This application is a continuation-in-part of Ser. No. 811,850 filed Dec. 20, 1985, now abandoned.

BACKGROUND OF THE INVENTION 3,6-Dichloropicolinic acid is a commercially useful herbicide (Johnston, U.S. Pat. No. 3,317,549) and 3,6-dichloro-2-(trichloromethyl)pyridine is known as a nitrification inhibitor (Goring, U.S. Pat. No. 3,135,594) and as a herbicide (Brett and Hodnett, U.S. Pat. No. 2,679,453). These compounds are not readily obtained by the pyridine ring chlorination of a 2-substituted pyridine because such chlorinations are not sufficiently selective to produce a preponderance of the desired 3,6-dichloro-2-substituted pyridine isomer in the mixture obtained. Alternative methods for introducing chlorine into the pyridine nucleus selectively at the 3 and 6 positions of 2-substituted pyridines depend upon the presence of amino or hydroxyl groups at those positions in the starting materials and the requisite materials are not commercially available.

A different approach to obtaining 3,6-dichloro-2-substituted pyridines which are convertible into 3,6-dichloropicolinic acid or 3,6-dichloro-2-(trichloromethyl)pyridine by simple known processes is to first prepare, from acyclic starting materials, a 2-hydrocarbyl-3,6-dichloropyridine. 2-Hydrocarbyl-3,6-dichloropyridines can be converted to 3,6-dichloropicolinic acid by oxidation using the general methods summarized in Abramovitch *Pyridine and its Derivatives* Supplement Part Two, pp 308-311 and Supplement Part Three, pp. 268-272. 3,6-Dichloro-2-methylpyridine can also be chlorinated to obtain 3,6-dichloro-2-(trichloromethyl)-pyridine using the methods described by Johnston and Tomita (U.S. Pat. No. 3,244,722). 3,6-Dichloro-2-(trichloromethyl)pyridine can be converted to 3,6-dichloropiecolinic acid by acid hydrolysis (U.S. Pat. No. 3,317,549).

SUMMARY OF THE INVENTION

It has now been found that 2-hydrocarbyl-3,6-dichloropyridines can be prepared by a ring closure method from readily available starting materials. A two step process is employed in which acrylonitrile and an appropriate dichloromethyl hydrocarbyl ketone are reacted under conditions conducive to the reaction to form a 1,1-dichloro-3-cyanopropyl hydrocarbyl ketone intermediate which is cyclized to obtain the desired 2-hydrocarbyl-3,6-dichloropyridine.

Briefly, in the process of the present invention acrylonitrile is first treated with an appropriate dichloromethyl hydrocarbyl ketone of Formula I in the presence of a base, such as an alkali metal alkoxide or hydroxide or a tertiary amine, to obtain a 1,1-dichloro-cyanopropyl hydrocarbyl ketone of Formula II. The reaction can be illustrated as follows:

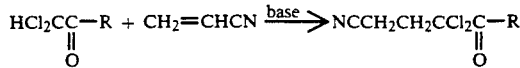

wherein R represents $C_1$-$C_8$ alkyl, $C_3$-$C_8$ cycloalkyl, or $C_4$-$C_8$ cycloalkylalkyl.

The 1,1-dichloro-3-cyanopropyl hydrocarbyl ketones of Formula II are then cyclized with hydrogen chloride to obtain 2-hydrocarbyl-3,6-dichloropyridines of Formula III. The reaction can be illustrated as follows:

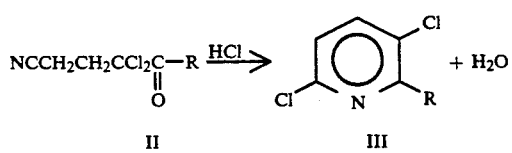

wherein R is as hereinbefore defined.

Both the intermediate 1,1-dichloro-3-cyanopropyl hydrocarbytl ketones of Formula II and the product 2-hydrocarbyl-3,6-dichloropyridines of Formula III are novel compounds.

The term hydrocarbyl as used herein is meant to designate the following moieties: alkyl including straight and branched chain isomers, cycloalkyl including those having alkyl substitutents (e.g. 2-methylcyclopropyl), and cycloalkylalkyl, such as cyclopentylmethyl.

DETAILED DESCRIPTION OF THE INVENTION

The addition reaction of a dichloromethyl hydrocarbyl ketone with acrylonitrile according to the present process is typically carried out in an organic solvent, such as t-butanol, ethanol, dimethylformamide, dimethyl sulfoxide, acetonitrile, methylene chloride, tetrahydrofuran, toluene, and the like. Reaction temperatures of from about 0° C. to about 120° C., preferably from about 40° to about 90°, are normally employed. The reaction mixture is usually agitated and it is often convenient to carry out the reaction at its reflux temperature.

Suitable bases for the addition reaction are those that are capable of abstracting a proton from the dichloromethyl hydrocarbyl ketone and include alkali metal hydroxides, such as sodium hydroxide or potassium hydroxide: alkali metal alkoxides, such as potassium t-butoxide or sodium ethoxide; and trialkylamines, such as triethylamine, N,N-dimethyl-N-hexylamine, N,N,N',N'-tetramethylethylenediamine, or N-methylpyrrolidine. When the base is an alkali metal hydroxide or alkali metal alkoxide, a quaternary ammonium salt, such as N,N,N-tricapryl-N-methylammonium chloride or N-benzyl-N,N,N-triethylammonium chloride, may be added to facilitate the reaction.

Approximately equimolar quantities of acrylonitrile and the dichloromethyl hydrocarbyl ketone or an excess of acrylonitrile can be conveniently employed in the process. The reaction is continued until a substantial amount of the desired 1,1-dichloro-3-cyanopropyl hydrocarbyl ketone product has formed or until one of the starting materials has been substantially depleted The exact time will depend on the starting dichloromethyl hydrocarbyl ketone employed as well as the solvent and the reaction temperature used.

The 1,1-dichloro-3-cyanopropyl hydrocarbyl ketones of Formula II prepared in the above described procedures can be recovered using conventional means, such as distillation, extraction, chromatography, crystallization, and the like. After recovery of the 1,1-dichloro-3-cyanopropyl hydrocarbyl ketones in a pure or partially purified form, they may be utilized in the cyclization reaction of the invention.

The cyclization reaction of 1,1-dichloro-3-cyanopropyl hydrocarbyl ketones is accomplished by heating these compounds in the presence of hydrogen chloride. The hydrogen chloride can be added to the reaction medium all at once or continuously during the reaction period. Metal chloride Lewis acid catalysts, such as zinc chloride and aluminum chloride can be employed along with the hydrogen chloride to facilitate this reaction. The reaction generates water and this may be removed as it forms by distillation, absorption, or reaction. Generally, anhydrous reactants are employed.

The cyclization reaction can be carried out neat or in the presence of an organic solvent, such as acetic acid, dimethylformamide, dimethyl sulfoxide, dioxane, dimethoxyethane, methylene chloride, toluene, and the like. Reaction temperatures of about 50° to about 200° C. and pressures of atmospheric to about 50 psi are advantageously employed The reaction is continued until a substantial amount of the 2-hydrocarbyl-3,6-dichloropyridine product is formed or until the 1,1-dichloro-3-cyanopropyl hydrocarbyl ketone reactant is substantially depleted The time required will vary depending upon the identity of the 1,1-dichloro-3-cyanopropyl hydrocarbyl ketone, the solvent, the concentration of hydrogen chloride and any Lewis acid catalysts, and the temperature employed The product 2-hydrocarbyl-3,6-dichloropyridines of Formula III can be recovered from the reaction medium by conventional means, such as distillation, extraction, chromatography, and the like.

Examples of dichloromethyl hydrocarbyl ketones useful as starting materials, 1,1-dichloro-3-cyanopropyl hydrocarbyl ketones obtained as intermediates, and 2-hydrocarbyl-3,6-dichloropyridines obtained as products in the present invention include those compounds of Formulas I, II, and III wherein R represents methyl, ethyl, propyl, 1-methylethyl, 1,1-dimethylethyl, butyl, hexyl, cyclohexyl, cyclopentyl, cyclooctyl, cyclopentylmethyl, cyclopropylmethyl, and the like. Compounds of Formulas I, II and III wherein R represents $C_1$–$C_4$ alkyl, $C_3$–$C_6$ cycloalkyl, or $C_4$–$C_6$ cycloalkylalkyl constitute a preferred class.

The following examples are merely illustrative of the process of this invention and should not be construed as limiting.

EXAMPLE 1

PREPARATION OF
4,4-DICHLORO-5-OXO-HEXANE-NITRILE

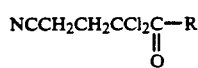

Procedure A

A mixture of 11 ml of t-butanol, 3 ml (31 mmol) of 1,1-dichloro-2-propanone and 2 ml (32 mmol) of acrylonitrile was placed in a 50 ml 3-necked round bottom flask equipped with a magnetic stirrer, a dropping funnel, a sampling port and a Y-tube fitted with a thermometer and an outlet to a scrubber. Four ml of 25 percent NaOH were added dropwise over 7 minutes, during which time the reaction exothermed to a final temperature of 71° C. After 68 minutes, with stirring, gas chromatographic (GC) analysis of the reaction mixture showed 40 percent unreacted 1.1-dichloro-2-propanone, 42 percent 4,4-dichloro-5-oxo-hexanenitrile, 10 percent 1,1-dichloro-2,4-cyclohexanedione, 2 percent 1-chloro-1-acetyl-2-cyanocyclopropane, and 1 percent 1,1,3,3-tetrachloro-2-methyl-4-oxo-2-pentanol.

An authentic sample of 4,4-dichloro-5-oxo-hexanenitrile, which was isolated by fractional distillation (b.p. 92°–95° C. at 0.1 mm Hg pressure) and purified by fractional crystallization (m.p. 49°–51° C.), analyzed as follows:

Analysis

|  | % C | % H | % N | % Cl |
| --- | --- | --- | --- | --- |
| Calc. for $C_6H_4Cl_2NO$: | 40.03 | 3.92 | 7.78 | 39.39 |
| Found: | 40.06 | 3.82 | 8.28 | 39.76 |

NMR (CDCl$_3$): δ2.56 (s,3H); δ2.72 (s,4H)

Procedure B

A 3.99 g (31.4 mmol) portion of 1,1-dichloro-2-propanone was dissolved in 8 ml of t-butanol and the mixture heated to 40° C. A solution of 1.61 g (30.3 mmol) of acrylonitrile in 3 ml of t-butanol and 10 ml of a 30 percent potassium hydroxide in methanol solution were added dropwise over 11 minute and 2.5 hour periods, respectively. The reaction was slow at first and the temperature fell to 25° C. The mixture was mildly warmed and after the bulk of the potassium hydroxide was added the reaction became exothermic and the temperature rose to a maximum of 75° C. After 4 hours the product mixture contained 40 percent 4,4-dichloro-5-oxo-hexanenitrile and 22 percent 1,1-dichloro-2-propanone by GC analysis.

Procedure C

A solution containing 8.0 g (63 mmol) of 1,1-dichloro-2-propanone and 3.2 g (61 mmol) of acrylonitrile and 0.73 g (7.2 mmol) of triethylamine in 20 ml of ethanol was prepared and heated to 56° C. over a 21 hour period. Another 1.46 g (14.4 mmol) of triethylamine was then added and the reaction continued for 3 additional hours. The reaction product was found to contain 17 percent 4,4-dichloro-5-oxo-hexanenitrile and 43 percent 1,1-dichloro-2-propanone by GC analysis.

EXAMPLE 2

PREPARATION OF
3,6-DICHLORO-2-METHYLPYRIDINE

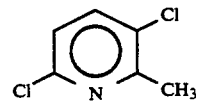

Procedure A

One g of 4,4-dichloro-5-oxo-hexanenitrile was placed in a 2-necked 10 ml pear shaped flask equipped with an HCl inlet and a Y-shaped tube attached to a NaOH scrubber and to a nitrogen inlet and holding a thermometer (touching the bottom of the flask). The flask was immersed in a silicone oil bath. HCl gas was bubbled through the 4,4-dichloro-5-oxo-hexanenitrile for 120 minutes during which time the temperature was maintained at 145°–160° C. A white solid condensate weighing 480 mg appeared in the Y-tube. GC analysis of the white condensate showed it to consist of about 50 percent 3,6-dichloro-2-methylpyridine and about 50 percent of a very high boiling material. GC analysis of the residue in the reaction flask showed it to consist of about 75 percent 4,4-dichloro-5-oxo-hexanenitrile and about 25 percent 3,6-dichloro-2-methylpyridine.

An authentic sample of 3,6-dichloro-2-methyl-pyridine, which was isolated by fractional distillation (b.p. 95° C. at 20 mm Hg pressure), analyzed as follows:
Analysis

|  | % C | % H | % N |
|---|---|---|---|
| Calc. for $C_6H_5Cl_2N$: | 44.5 | 3.1 | 8.6 |
| Found: | 44.9 | 3.2 | 9.0 |

NMR (CDCl$_3$): $\delta$2.60 (s,3H), $\delta$7.17 (d-7.6 Hz, 1H), $\delta$7.64 (d-7.6 Hz, 1H)

Procedure B

A 1.11 g sample of 4,4-dichloro-5-oxohexane-nitrile was placed in an 8 oz pressure bottle and pressurized to 15 psi with hydrogen chloride gas. The bottom portion of the bottle was heated in a silicone oil bath to a maximum of 197° C. for 30 minutes and at 110°–155° for another 6 hours. After cooling the reaction mixture was diluted with methanol, filtered, basified and extracted with methylene chloride to obtain a product that was 45 percent 3,6-dichloro-2-methylpyridine by GC analysis.

Acrylonitrile is an item of commerce and readily available. Dichloromethyl hydrocarbyl ketones of Formula I are generally known in the art. They can be prepared from the corresponding methyl hydrocarbyl ketones by the formation of an amino derivative and subsequent chlorination of that derivative with N-chlorosuccinimide as described in Bull. Soc. Chim. Belg., 81, 643-7 (1972).

We claim:

1. A method for preparing 2-hydrocarbyl-3,6-cichloropyridine compounds of the formula

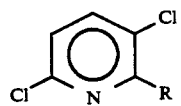

wherein R represents $C_1$–$C_{18}$ alkyl, $C_3$–$C_8$ cycloalkyl, or $C_4$–$C_8$ cycloalkylalkyl, which comprises reacting, in the presence of a base capable of abstracting a proton from a dichloromethyl hydrocarbyl ketone, acrylonitrile and a dichloromethyl hydrocarbyl ketone of the formula

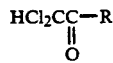

wherein R is defined as before, under conditions conducive to the reaction, obtaining an intermediate 1,1-cichloro-3-cyanopropyl hydrocarbyl ketone compound of the formula

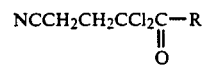

wherein R is defined as before, acidifying the intermediate with hydrogen chloride, heating the acidified intermediate at temperatures between about 50° C. and about 200° C., and, thereafter, recovering the 2-hydrocarbyl-3,6-dichloropyridine compound.

2. A method as recited in claim 1 wherein the base is a trialkylamine.

3. A method as recited in claim 1 wherein the base is an alkali metal $C_1$–$C_4$ alkoxide.

4. A method as recited in claim 1 wherein the base is an alkali metal hydroxide.

5. A method as recited in claim 1 wherein R is $C_1$–$C_4$ alkyl, $C_3$–$C_6$ cycloalkyl, or $C_4$–$C_6$ cycloalkylalkyl.

6. A method as recited in claim 5 wherein R is methyl.

7. A 1,1-dichloro-3-cyanopropyl hydrocarbyl ketone compound of the formula

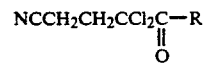

wherein R represents $C_1$–$C_8$ alkyl, $C_3$–$C_8$ cycloalkyl, or $C_4$–$C_8$ cycloalkylalkyl.

8. A compound of claim 7 wherein R is $C_1$–$C_4$ alkyl, $C_3$–$C_6$ cycloalkyl, or $C_4$–$C_6$ cycloalkylalkyl.

9. A compound of claim 8 wherein R is methyl.

10. A method for preparing 1,1-dichloro-3-cyanopropyl hydrocarbyl ketone compounds of the formula

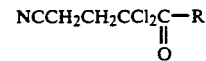

wherein R represents $C_1$–$C_8$ alkyl, $C_3$–$C_8$ cycloalkyl, or $C_4$–$C_8$ cycloalkylalkyl, which comprises reacting, in the presence of a base capable of abstracting a proton from a dichloromethyl hydrocarbyl ketone, acrylonitrile and a dichloromethyl hydrocarbyl ketone of the formula

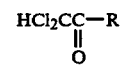

wherein R is as defined before, under conditions conducive to the reaction and, thereafter, recovering said compound.

11. A method as recited in claim 10 wherein the base is a trialkylamine.

12. A method as recited in claim 10 wherein the base is an alkali metal $C_1$–$C_4$ alkoxide.

13. A method as recited in claim 10 wherein the base is an alkali metal hydroxide.

14. A method as recited in claim 10 wherein R is $C_1$–$C_4$ alkyl, $C_3$–$C_6$ cycloalkyl or $C_4$–$C_6$ cycloalylkalkyl.

15. A method as recited in claim 14 wherein R is methyl.

16. A method for preparing 2-hydrocarbyl-3,6-dichloropyridine compounds of the formula

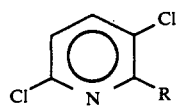

wherein R represents $C_1$-$C_8$ alkyl, $C_3$-$C_8$ cycloalkyl, or $C_4$-$C_8$ cycloalkylalkyl, which comprises acidifying a compound of the formula

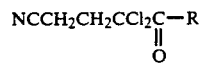

wherein R is defined as before, with hydrogen chloride, heating the acidified compound at a temperature between about 50° C. and about 200° C., and, thereafter, recovering the 2-hydrocarbyl-3,6-dichloropyridine compound.

17. A method as recited in claim 16 wherein R is $C_1$-$C_4$ alkyl, $C_3$-$C_6$ cycloalkyl, or $C_4$-$C_6$ cycloalkylalkyl.

18. A method as recited in claim 17 wherein R is methyl.

* * * * *